United States Patent [19]

Axen et al.

[11] 4,337,337

[45] Jun. 29, 1982

[54] 2,5-INTER-O-PHENYLENE-3,4-DINOR-5,9α-EPOXY-6-IODO-PGF$_1$ COMPOUNDS

[75] Inventors: Udo F. Axen, Plainwell; John C. Sih, Kalamazoo, both of Mich.

[73] Assignee: The Upjohn Company, Kalamazoo, Mich.

[21] Appl. No.: 165,834

[22] Filed: Jul. 3, 1980

Related U.S. Application Data

[60] Division of Ser. No. 62,443, Jul. 31, 1979, Pat. No. 4,312,810, which is a continuation-in-part of Ser. No. 962,845, Nov. 22, 1978, abandoned.

[51] Int. Cl.$^3$ .......................................... C07D 311/00
[52] U.S. Cl. .................................. 542/426; 542/429; 549/396

[58] Field of Search ..................... 260/345.2; 542/426, 542/429

[56] References Cited

U.S. PATENT DOCUMENTS 4,123,441  10/1978  Johnson ........................... 260/345.2

Primary Examiner—Nicky Chan
Attorney, Agent, or Firm—Robert A. Armitage

[57] ABSTRACT

The present invention provides 2,5-inter-o-phenylene-3,4-dinor-6,9α-epoxy-6β-6-iodo-PGF$_1$ compounds. These compounds are intermediates for preparing 2,5-inter-o-phenylene-3,4-dinor-prostacyclin analogs, which are useful for pharmacological purposes, e.g., as antithrombotic agents.

1 Claim, No Drawings

2,5-INTER-O-PHENYLENE-3,4-DINOR-5,9α-EPOXY-6-IODO-PGF₁ COMPOUNDS

CROSS REFERENCE TO RELATED APPLICATION

This application is a division of Ser. No. 062,443, now U.S. Pat. No. 4,312,810 filed July 31, 1979, which is a continuation-in-part of Ser. No. 962,845, filed Nov. 22, 1978, now abandoned.

BACKGROUND OF THE INVENTION

The present invention relates to novel prostacyclin analogs and intermediates for their production. In particular, the present invention relates to prostacyclin intermediates useful in the production of 2,5-inter-o-phenylene-3,4-dinor-prostacyclin analogs. Most particularly the present invention provides 2,5-inter-o-phenylene-3,4-dinor-5,9α-epoxy-6-iodo-PGF₁ compounds. The preparation and use of the novel compounds described herein is incorporated here by reference U.S. Pat. No. 4,281,113.

SUMMARY OF THE INVENTION

The present invention particularly provides a prostacyclin intermediate of formula IX

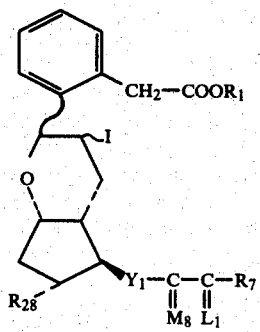

wherein $R_{28}$ is $-OR_{10}$, $-CH_2OR_{10}$, hydroxy, hydroxymethyl, or hydrogen, wherein $R_{10}$ is a blocking group removable by mild acidic hydrolysis; wherein $Y_1$ is
(1) trans—CH=CH—,
(2) cis—CH=CH—,
(3) —CH₂CH₂—, or
(4) —C≡C—,
wherein $M_8$ is $\alpha$-$R_5$:$\beta$-$OR_{10}$ or $\alpha$-$OR_{10}$:$\beta$-$R_5$, wherein $R_5$ is hydrogen or methyl and $R_{10}$ is as defined above, or
$\alpha$-$R_5$:$\beta$-OH or $\alpha$-OH:$\beta$-$R_5$, wherein $R_5$ is as defined above;
wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$-$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is
(1) —(CH₂)$_m$—CH₃, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $R_1$ is
(1) hydrogen;
(2) alkyl of one to 12 carbon atoms, inclusive;
(3) cycloalkyl of 3 to 10 carbon atoms, inclusive;
(4) aralkyl of 7 to 12 carbon atoms, inclusive;
(5) phenyl;
(6) phenyl substituted with one, 2 or 3 chloro or akyl of one to 3 carbon atoms; or
(7) phenyl substituted in the para position by
 (a) —NH—CO—$R_{25}$
 (b) —CO—$R_{26}$
 (c) —O—CO—$R_{27}$
 (d) —CH=N—NH—CO—NH₂
wherein $R_{25}$ is methyl, phenyl, acetamidophenyl, benzamidophenyl, or —NH₂; $R_{26}$ is hydrogen, methyl, phenyl, —NH₂, or methoxy; and $R_{27}$ is phenyl or acetamidophenyl, inclusive, or a pharmacologically acceptable salt thereof when $R_1$ is hydrogen.

The novel prostaglandin analogs prepared from the above intermediates are useful for a variety of prostacyclin-like pharmacological purposes, particularly and especially as inhibitors of platelet aggregation in vivo and in vitro. Thus, these prostacyclin analogs are useful for a variety of pharmacological and therapeutical purposes, e.g., as antithrombotic agents.

We claim:
1. A prostacyclin intermediate of formula IX

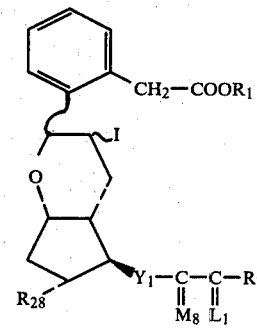

wherein $R_{28}$ is $-OR_{10}$, $-CH_2OR_{10}$, hydroxy, hydroxymethyl, or hydrogen, wherein $R_{10}$ is a blocking group removable by mild acidic hydrolysis;
wherein $Y_1$ is
(1) trans—CH=CH—,
(2) cis—CH=CH—,
(3) —CH₂CH₂—, or (4) —C≡C—, wherein $M_8$ is $\alpha$-$R_5$:$\beta$-$OR_{10}$ or $\alpha$-$OR_{10}$:$\beta$-$R_5$, wherein $R_5$ is hydrogen or methyl and $R_{10}$ is as defined above, or $\alpha$-$R_5$:$\beta$-OH or $\alpha$-OH:$\beta$-$R_5$, wherein $R_5$ is as defined above;

wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;

wherein $R_7$ is (1) —$(CH_2)_m$—$CH_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;

wherein $R_1$ is (1) hydrogen;
(2) alkyl of one to 12 carbon atoms, inclusive;
(3) cycloalkyl of 3 to 10 carbon atoms, inclusive;
(4) aralkyl of 7 to 12 carbon atoms, inclusive;
(5) phenyl;
(6) phenyl substituted with one, 2 or 3 chloro or alkyl of one to 3 carbon atoms; or
(7) phenyl substituted in the para position by
  (a) —NH—CO—$R_{25}$
  (b) —CO—$R_{26}$
  (c) —O—CO—$R_{27}$
  (d) —CH=N—NH—CO—$NH_2$ wherein $R_{25}$ is methyl, phenyl, acetamidophenyl, benzamidophenyl, or —$NH_2$; $R_{26}$ is hydroxy, methyl, phenyl, —$NH_2$, or methoxy; and $R_{27}$ is phenyl or acetamidophenyl, inclusive, or a pharmacologically acceptable salt thereof when $R_1$ is hydrogen.

* * * * *

UNITED STATES PATENT OFFICE
CERTIFICATE OF CORRECTION

Patent No. 4,337,337  Dated 6-29-82

Inventor(s) Axen, U.F. and Sih, J.C.

It is certified that error appears in the above-identified patent and that said Letters Patent are hereby corrected as shown below:

Column 2, line 33 reads --$R_{26}$ is hydrogen, methyl,-- should read "$R_{26}$ is hydroxy, methyl,"

Signed and Sealed this

Fourteenth Day of September 1982

[SEAL]

Attest:

Attesting Officer

GERALD J. MOSSINGHOFF

Commissioner of Patents and Trademarks